| United States Patent [19] | [11] Patent Number: 4,975,216 |
|---|---|
| Schluessler | [45] Date of Patent: Dec. 4, 1990 |

[54] SHORT-CHAIN ALKANE SULFONIC ACIDS IN CLEANING PREPARATIONS AND DISINFECTANTS

[75] Inventor: Hans-Joachim Schluessler, Haan, Fed. Rep. of Germany

[73] Assignee: Ecolab, Inc., St. Paul, Minn.

[21] Appl. No.: 384,861

[22] Filed: Jul. 21, 1989

Related U.S. Application Data

[63] Continuation of Ser. No. 128,960, Dec. 4, 1987, abandoned.

[30] Foreign Application Priority Data

Dec. 13, 1986 [DE] Fed. Rep. of Germany ....... 3642604

[51] Int. Cl.$^5$ .......................... A61L 2/16; C11D 3/48; C11D 7/08; C11D 7/34
[52] U.S. Cl. ....................................... 252/106; 134/3; 134/4; 156/666; 252/79.4; 252/136; 252/142; 252/146; 252/535; 252/554; 252/DIG. 14; 422/28
[58] Field of Search ....................... 134/3, 4; 156/666; 252/79.4, 136, 142, 535, 554, 106

[56] References Cited

U.S. PATENT DOCUMENTS

| 3,351,555 | 11/1967 | Byers | 252/79.2 |
|---|---|---|---|
| 3,653,997 | 4/1972 | Rothschild | 156/666 |
| 3,905,907 | 9/1975 | Shiga | 252/79.4 |
| 3,953,263 | 4/1976 | Ishikawa | 156/666 |
| 4,215,005 | 7/1980 | Hay | 252/153 |
| 4,439,338 | 3/1984 | Tomaiuolo | 252/79.1 |
| 4,541,944 | 9/1985 | Sanderson | 252/95 |
| 4,632,727 | 12/1986 | Nelson | 156/656 |
| 4,695,348 | 9/1987 | Battey | 156/647 |

FOREIGN PATENT DOCUMENTS

2130877 7/1973 France .
1562961 3/1980 United Kingdom .

OTHER PUBLICATIONS

Ullmanns Encyklopadie der technischen Chemie, 4th Edition, vol. 20, pp. 153 et seq.

*Primary Examiner*—Dennis Albrecht
*Attorney, Agent, or Firm*—Ernest G. Szoke; Wayne C. Jaeschke; Henry E. Millson

[57] ABSTRACT

Short-chain alkane sulfonic acids containing from 1 to 4 carbon atoms or mixtures thereof as sole acid component of cleaning preparations and/or disinfectants, optionally together with other inorganic or organic acids, particularly for use in the food-processing industry.

2 Claims, No Drawings

SHORT-CHAIN ALKANE SULFONIC ACIDS IN CLEANING PREPARATIONS AND DISINFECTANTS

This application is a continuation of application Ser. No. 128,960, filed Dec. 4, 1987, now abandoned.

BACKGROUND OF THE INVENTION

1. Field of the Invention

This invention relates to alkane sulfonic acids in cleaning preparations and/or disinfectants, more especially in the food-processing industry.

2. Statement of Related Art

In the field of cleaning and disinfection, products based on nitric acid, sulfuric acid and phosphoric acid are at present used for all applications where acidic preparations are indicated. Mixtures of these acids are also used for special applications. Hydrochloric acid and hydrofluoric acid are only used in particular cases where the material to be cleaned is not endangered by corrosion.

Accordingly, only the first three mineral acids set forth above are used for cleaning and disinfection in the food-processing industry. Besides its function as an acid, phosphoric acid in particular shows cleaning active effects. Accordingly, it is used to a predominant extent in the field of cleaning and disinfection.

The list of acids should be completed by a number of organic acids, particularly amidosulfonic acid, formic acid, in some cases acetic acid, and citric acid. On account of their weaker acidity, however, they cannot be universally used. The corresponding acidic salts of the above inorganic and organic acids are of course also used. Phosphoric acid and its acidic salts are still being used to a predominant extent as the basis for acidic cleaning preparations and/or disinfectants. The phosphoric acid or its salts are combined with surfactants, foam inhibitors, corrosion inhibitors and, optionally, solution promoters, and also with special disinfection components which are stable and active in the phosphoric acid medium, for example quaternary ammonium compounds, elemental iodine, hydrogen peroxide and other per compounds.

These combinations are used at temperatures of from 5° to 85° C. to remove protein, fat and mineral soil of the type encountered in the corresponding branches of the food-processing industry. Products based on sulfuric acid and nitric acid are also commercially available for removing soil of a purely mineral nature. Sulfuric and nitric acid may also be combined with special disinfection components which are stable and active therein.

Due to the recently increasing need to replace nitrate-containing and, generally, nitrogen-containing products and especially products based on phosphoric acid by other acid bases for environmental reasons, a number of basic studies has shown that only limited possibilities are available for replacing either nitric acid or phosphoric acid. Sulfuric acid for example, which might be considered as a replacement, cannot be used for removing such soil as, for example, carbohydrates, protein, fats, inorganic material constituents and other residues due to its inadequate cleaning effect with respect to organic soil. In addition, sulfuric acid has a highly corrosive effect on chrome-nickel steels and aluminium surfaces, particularly at relatively high temperatures of around 85° C.

One possible solution to this problem is the use of amidosulfonic acid, which has a good cleaning effect with respect to organic soil and which, in terms of corrosion, is acceptable for chrome nickel steel and aluminium.

In so-called standing baths, i.e. cleaning baths of the type predominantly used for repeatedly carrying out a cleaning and/or disinfection process, amidosulfonic acid undergoes decomposition. The cleaning effect then becomes inadequate and, in addition, corrosion occurs. In most cases, the organic acids known from the prior art are ineffectual, particularly with respect to inorganic soil (short-chain carboxylic acids and dicarboxylic acids), or have too strong an odor during the cleaning process (formic acid).

Ullmanns Encyklopadie der technischen Chemie, 4th Edition, Vol. 20, pages 153 et seq. describes cleaning preparations and disinfectants for the food industry and lists the constituents typical of such preparations.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide an improved cleaning preparation and/or disinfectant which is low in or rather free from nitrogen and phosphorus to meet environmental requirements and which is particularly suitable for the removal of soil such as, for example, carbohydrates, protein, fats, inorganic mineral constituents and other remains in the food-processing industry. At the same time, the cleaning preparation and/or disinfectants of the invention are intended to leave chrome-nickel steels, aluminium and copper surfaces free from corrosion at temperatures of up to 85° C., e.g. from ambient temperatures up to 85° C., preferably at a temperature of from 40° C. to 85° C.

It has surprisingly been found that the use of certain alkane sulfonic acids in cleaning preparations and/or disinfectants affords advantages in the removal of the soil types discussed above.

It has been found that, in addition to their effectiveness against organic soil types, alkane sulfonic acids containing from 1 to 4 carbon atoms are also capable, by virtue of their high acidity, of removing mineral soils. In addition, it has been found that, in contrast to the use of sulfuric acid, there is no sign of the corrosion produced by known cleaning preparations in chromenickel steels, even at high temperatures.

Alkyl or aryl sulfonic acids having longer chains develop little or no cleaning activity in cleaning preparations or are unuseable due to their high foaming power.

According to the invention, therefore, short-chain alkane sulfonic acids containing from 1 to 4 carbon atoms are employed in the cleaning and/or disinfectant compositions of the invention. Hence, in the context of the invention, alkane sulfonic acids are understood to include methane sulfonic acid, ethane sulfonic acid, n- and i-propane sulfonic acid and n-, i- and tert.-butane sulfonic acid. It is preferred to use methane sulfonic acid, ethane sulfonic acid and/or a butane sulfonic acid. According to the invention, the alkane sulfonic acids can be used either individually or in the form of mixtures in cleaning preparations and/or disinfectants.

The alkane sulfonic acids of the invention are used in concentrations of from 0.5 to 100% by weight and preferably in concentrations of from 5 to 95% by weight in the cleaning preparations and disinfectants of the invention.

Accordingly, cleaning preparations and disinfectants containing short-chain sulfonic acids which are free from nitrogen (nitrate) and phosphorus (phosphate) and which, in addition, are not corrosive to chrome-nickel steel fall within the scope of the present invention. Where the phosphorus content is of only minor significance, the acidic cleaning preparations and disinfectants can also contain, in addition to the alkane sulfonic acids, phosphoric acid or sulfuric acid and, optionally, organic acids as a mixed acid base. In that case, from 30% to 40% sulfuric acid and/or 20 to 30% phosphoric acid may advantageously be present in addition to the alkane sulfonic acids.

In addition to the acids mentioned above, the cleaning preparations containing alkane sulfonic acids may optionally contain other soil-digesting components, complexing agents, surfactants, corrosion inhibitors, foam inhibitors and perfumes, as described for example in Ullmanns Encyklopadie der technischen Chemie, 4th Edition, Vol. 20, pages 153 et seq. which is incorporated herein by reference.

Disinfectants in the context of the present invention may contain, for example, peroxy compounds, iodophores, quaternary ammonium compounds, ampholytes and aldehydes, as described for example in Ullmanns loc.. cit., page 155.

The invention will be illustrated but not limited by the following examples.

EXAMPLES

Corrosion behavior of the alkane sulfonic acids 0.5% solutions of methane, propane, butane and octane sulfonic acids and sulfuric acid in water (0° Gh) were prepared and subjected to a corrosion test against chrome-nickel steel plates (4401; 10×5 cm) at 75° C. in accordance with DIN 50 905. After a contact time of 24 hours on the chrome-nickel steel plates, the following weight losses were measured:

| | | |
|---|---|---|
| Methane sulfonic acid | 0.13 g/m$^2$ | (0.0054 g/m$^2$.h) |
| Propane sulfonic acid | 0.41 g/m$^2$ | (0.017 g/m$^2$.h) |
| Butane sulfonic acid | 0.44 g/m$^2$ | (0.018 g/m$^2$.h) |
| Octane sulfonic acid | 4.74 g/m$^2$ | (0.20 g/m$^2$.h) |
| Sulfuric acid | 9.53 g/m$^2$ | (0.40 g/m$^2$.h) |

The corrosion test clearly shows that, under the above conditions, chrome-nickel steel is attacked to a significant extent by octane sulfonic acid and sulfuric acid. According to the resistance tables, the erosion produced by methane, propane and butane sulfonic acid is regarded as completely resistant (erosion up to 0.03 g/m$^2$.h). The erosion values of octane sulfonic acid and sulfuric acid are of a level which can no longer be accepted because the roughening of the surface is too great and cleaning is complicated. In addition, there is a risk of pitting under certain external in-use conditions, such as for example a high chloride content of the water. In addition, erosion is considerably higher and counts as "not very resistant" or "not resistant" when the temperature of the cleaning and/or disinfectant solutions is above 75° C., as is the case for example in ultrahigh temperature processes (up to 140° C.).

Foaming Behavior

In a Gotte foam beater (DIN 53 902, Part 1), methane, ethane, propane, butane, n-hexane and n-octane sulfonic acid were tested for their foaming behavior in 0.5% aqueous solution (0° Gh) at 40° C. The solutions of methane, ethane, propane and butane sulfonic acid did not produce any foam.

Hexane sulfonic acid produced 10 ml and octane sulfonic acid 250 ml of a stable foam which had not collapsed after 10 seconds.

EXAMPLE 1

100 cm$^3$ glass bottles were semi-immersed in condensed milk, the milk was allowed to drain off and the bottles were subsequently left standing over sodium sulfate in an exsiccator for 24 hours at 20° C. to dry. The bottles thus prepared were immersed in the solution to be tested by means of an immersion apparatus and removed again. This immersion process was repeated until the soil had been removed from the glass bottle. The average immersion time of the immersion process was 5 seconds.

The 100 cm$^3$ bottles were immersed in an aqueous solution (0° Gh) of 0.5% methane sulfonic acid at 50° C. After 8 immersions, the soil had been removed from the glass surface.

COMPARISON EXAMPLE 1

100 cm$^3$ glass bottles which had been prepared in accordance with Example 1 were immersed as in Example 1 in 0.5% aqueous (0° Gh) sulfuric acid. This solution did not show any cleaning effect at all.

EXAMPLE 2

Bottles prepared in the same way as in Example 1 were subjected to a certain number of immersions (30), after which the cleaning effect was visually assessed. In this method, a cleaning solution consisting of:

0.5% ethane sulfonic acid,
0.15% of an ethoxylated (9 EO) fatty alcohol ($C_{10}$–$C_{18}$) as degreasing component,
0.1% of a polyethylene glycol ether ($C_8$–$C_{18}$ alkyl radical, 9 EO groups with butyl termination) as anti-foam component, and
remainder water was used in an immersion apparatus comprising 6 immersion baths. After 30 immersions, the solution containing ethane sulfonic acid showed a satisfactory cleaning effect.

EXAMPLE 3

Instead of the solution used in Example 2, a corresponding solution containing 0.5% n-propane sulfonic acid was used for the immersion tests. After 30 immersions, the solution containing propane sulfonic acid showed a satisfactory cleaning effect.

EXAMPLE 4

Instead of the solution used in Example 2, a corresponding solution containing 0.5% n-butane sulfonic acid is used for the immersion tests. After 30 immersions, the solution containing n-butane sulfonic acid showed a satisfactory cleaning effect.

COMPARISON EXAMPLE 2

Instead of the solution used in Example 2, a corresponding solution containing 0.5% hexane sulfonic acid was used for the immersion tests. After 30 immersions, the solution containing hexane sulfonic acid showed hardly any cleaning effect.

COMPARISON EXAMPLE 3

Instead of the solution used in Example 2, a corresponding solution containing 0.5% octane sulfonic acid was used for the immersion tests. After 30 immersions, the solution containing octane sulfonic acid showed hardly any cleaning effect.

COMPARISON EXAMPLE 4

Instead of the solution used in Example 2, a corresponding solution containing 0.5% sulfuric acid was used for the immersion tests. After 30 immersions, the solution containing sulfuric acid showed hardly any cleaning effect.

EXAMPLE 5

In a milk heater circuit consisting of milk and cream heater, centrifuge, milk tank and pipe system, the acidic phase which, previously, had been run with a product containing nitric acid in a concentration of 2% at 80° C. was run with a 1% acidic solution consisting of n-propane sulfonic acid after preliminary alkaline cleaning. The cleaning effect (elimination of milk scale) was satisfactory. Even after a prolonged period, no sign of corrosion could be detected on the chrome-nickel steel plates (4301) or on the sealing material.

EXAMPLE 6

Fermentation tanks were operated with satisfactory results for about 1 hour at 6° C. with a product based on phosphoric acid in combination with an ethoxylation product of a $C_{12}$–$C_{14}$ fatty acid and anti-foam agent. The tanks were cleaned from the spray head of a mixing vessel provided for the cleaning preparation and/or disinfectant. A mixture of butane and methane sulfonic acid was used instead of the phosphoric acid product, containing the same ethoxylation and anti-foam additives. The cleaning result was distinctly better than in the method described above. The cleaning time was reduced to 45 minutes.

I claim:

1. An aqueous acidic cleaning and disinfectant composition consisting of
   A. a cleaning and disinfecting quantity of at least one $C_1$–$C_4$ alkane sulfonic acid;
   B. from 30 to about 40% by weight of sulfuric acid and/or from about 20 to about 30% by weight of phosphoric acid; and, optionally,
   C. at least one of another soil-digesting component, another disinfectant, a complexing agent, a surfactant, a corrosion inhibitor, a foam inhibitor, and a perfume; and;
   D. balance water:
wherein component B is the only inorganic acid component of the composition.

2. The composition of claim 1 wherein in component A the at least one $C_1$–$C_4$ alkane sulfonic acid is one or more of methane sulfonic acid, ethane sulfonic acid, n-propane sulfonic acid, and n-butane sulfonic acid.

* * * * *